United States Patent
Teodorczyk et al.

(10) Patent No.: US 7,291,256 B2
(45) Date of Patent: Nov. 6, 2007

(54) MEDIATOR STABILIZED REAGENT COMPOSITIONS AND METHODS FOR THEIR USE IN ELECTROCHEMICAL ANALYTE DETECTION ASSAYS

(75) Inventors: Maria Teodorczyk, San Jose, CA (US); Ronald C. Chatelier, Bayswater (AU); Alastair McIndoe Hodges, Blackburn South (AU); Timothy Ohara, Danville, CA (US); Remy Dato, Pleasanton, CA (US)

(73) Assignee: Lifescan, Inc., Milpitas, CA (US)

( * ) Notice: Subject to any disclaimer, the term of this patent is extended or adjusted under 35 U.S.C. 154(b) by 427 days.

(21) Appl. No.: 10/242,951

(22) Filed: Sep. 12, 2002

(65) Prior Publication Data
US 2004/0050717 A1   Mar. 18, 2004

(51) Int. Cl.
*G01N 27/327* (2006.01)

(52) U.S. Cl. .............................. 205/777.5; 204/403.14; 435/14; 435/25; 435/26

(58) Field of Classification Search ..............................
204/401.01–401.14, 403.01–403.14; 205/775, 205/778, 777.5, 792; 435/4–28
See application file for complete search history.

(56) References Cited

U.S. PATENT DOCUMENTS

| | | | |
|---|---|---|---|
| 4,224,125 A | 9/1980 | Nakamura et al. | |
| 4,545,382 A | 10/1985 | Higgins et al. | |
| 5,004,583 A * | 4/1991 | Guruswamy et al. | 422/58 |
| 5,266,179 A | 11/1993 | Nankai et al. | |
| 5,421,981 A * | 6/1995 | Leader et al. | 204/403.13 |
| 5,723,284 A | 3/1998 | Ye | |
| 5,834,224 A | 11/1998 | Ruger et al. | |
| 5,942,102 A | 8/1999 | Hodges et al. | |
| 5,972,199 A | 10/1999 | Heller et al. | |
| 5,997,817 A | 12/1999 | Crismore et al. | |
| 6,059,946 A | 5/2000 | Yukawa et al. | |
| 6,083,710 A | 7/2000 | Heller et al. | |
| 6,121,009 A | 9/2000 | Heller et al. | |
| 6,134,461 A | 10/2000 | Say et al. | |
| 6,179,979 B1 | 1/2001 | Hodges et al. | |
| 6,193,873 B1 | 2/2001 | Ohara et al. | |
| 6,284,125 B1 | 9/2001 | Hodges et al. | |
| 6,558,528 B1 * | 5/2003 | Matzinger | 205/777.5 |

(Continued)

FOREIGN PATENT DOCUMENTS

EP   0 969 097 A2   1/2000

(Continued)

OTHER PUBLICATIONS

Table 8.8, Record No. 57 of Lange's Handbook of Chemistry (15th ed). 1999.*

(Continued)

*Primary Examiner*—Alex Noguerola

(57) ABSTRACT

Mediator stabilized reagent compositions and methods for their use in electrochemical analyte determination assays are provided. The subject reagent compositions include an enzyme, a redox mediator and a mediator-stabilizing buffer. Optionally, the reagent compositions may further include one or more of a wetting agent, detergent, enzyme cofactor and combinations thereof. Also provided are electrochemical test strips that include the subject reagent compositions, systems and kits that include the same as well as methods for using the same in analyte detection assays. The subject invention finds use in a variety of different applications, including glucose concentration determination applications.

23 Claims, 10 Drawing Sheets

U.S. PATENT DOCUMENTS

| | | | |
|---|---|---|---|
| 6,632,349 B1 * | 10/2003 | Hodges et al. | 205/792 |
| 6,638,415 B1 * | 10/2003 | Hodges et al. | 205/775 |
| 6,773,564 B1 * | 8/2004 | Yugawa et al. | 204/403.14 |
| 6,946,067 B2 * | 9/2005 | Hodges et al. | 205/792 |
| 2002/0179442 A1 * | 12/2002 | Miyazaki et al. | 204/403.01 |

FOREIGN PATENT DOCUMENTS

| | | |
|---|---|---|
| EP | 1 146 332 | 10/2001 |
| EP | 1 239 048 | 9/2002 |
| GB | 2304628 A | 8/1995 |
| JP | 3403378 | 2/2003 |
| WO | WO97/18465 | 5/1997 |
| WO | WO99/49307 | 9/1999 |
| WO | WO 01/57238 A2 | 8/2001 |
| WO | WO 01/57510 A2 | 8/2001 |
| WO | WO 01/73419 A1 * | 10/2001 |
| WO | WO 02/48707 A2 | 6/2002 |
| WO | WO 02/50609 A2 | 6/2002 |

OTHER PUBLICATIONS

"pKa data Compiled by R. Williams" downloaded from research.chem.psu.edu/brgroup/pKa_compilation.pdf, Jun. 2, 2006.*

Buffer solution entry in Concise Encyclopedia of Chemistry Walter de Gruyter Berlin—New York 1994.*

Table 8.8, Record No. 551 of Lange's Handbook of Chemistry (15th ed.), 1999.*

Table 8.8, Record No. 1979 of Lange's Handbook of Chemistry (15th ed.), 1999.*

Table 8.8, Record No. 1856 of Lange's Handbook of Chemistry (15th ed.), 1999.*

Table 8.8, Record No. 1116 of Lange's Handbook of Chemistry (15th ed.), 1999.*

English language translation of Miyazaki et al. (WO 01/73419 A1), Oct. 4, 2001.*

H.A. Saroff, "Ionization of Clusters," Archives of Biochemistry and Biophysics, vol. 256, No. 1, Jul. pp. 110-130, 1987.

European equivalent of Publication CN1365446, Shoji Miyazaki, et al. Matsushia Electric Ind Co Ltd., "Biosensor" 2502-06-21.

* cited by examiner

Linearity Test Comparing Citrate, Malic and Tartaric Acid Formulations

MEDIATOR STABILIZED REAGENT COMPOSITIONS AND METHODS FOR THEIR USE IN ELECTROCHEMICAL ANALYTE DETECTION ASSAYS

INTRODUCTION

1. Field of the Invention

The field of this invention is analyte determination, particularly electrochemical analyte determination and more particularly the electrochemical determination of blood analytes.

2. Background

Analyte detection in physiological fluids or samples, e.g., blood or blood derived products, is of ever increasing importance to today's society. Analyte detection assays find use in a variety of applications, including clinical laboratory testing, home testing, etc., where the results of such testing play a prominent role in the diagnosis and management of a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a reaction zone in an electrochemical cell comprising at least two electrodes, i.e., a reference and working electrode, where the electrodes have an impedance which renders them suitable for amperometric measurement. The component to be analyzed is allowed to react directly with an electrode, or directly or indirectly with a redox reagent to form an oxidizable (or reducible) substance in an amount corresponding to the concentration of the component to be analyzed, i.e., analyte. The quantity of the oxidizable (or reducible) substance present is then estimated electrochemically and related to the amount of analyte present in the initial sample.

In many such electrochemical approaches to analyte detection, an analyte oxidizing signal producing system comprising an enzyme component and a mediator component is employed, where the enzyme component oxidizes the analyte of interest and then transfers an electron to a mediator which, in turn, transfers the electron to an electrode in the electrochemical cell, thereby generating an electrical signal from which the analyte concentration can be determined.

In electrochemical test strips, the strips are typically manufactured at some time prior to their use. Between their manufacture and use, the test strips are stored. During this storage period, a proportion of the mediator can transform to its reduced from. In such situations, inaccurate results may be obtained when the strip is finally employed because some of the mediator is already reduced.

As such, there is interest in the development of electrochemical reagent formulations in which the mediator is storage stabilized. The present invention satisfies this need.

Relevant Literature

U.S. Pat. Nos.: 5,723,284; 5,834,224; 5,942,102; 5,972,199; 5,997,817; 6,059,946; 6,083,710; 6,121,009; 6,134,461; 6,179,979; 6,193,973 and 6,284,125; as well as other patent documents: WO 99/49307; WO 97/18465; WO 01/57510; WO 01/57238; WO 02/48707; WO 02/50609; EP 0 969 097A2; JP091403378A; and GB 2 304 628.

SUMMARY OF THE INVENTION

Mediator stabilized reagent compositions and methods for their use in electrochemical analyte determination assays are provided. The subject reagent compositions include an enzyme, a redox mediator and a mediator-stabilizing buffer. Optionally, the reagent compositions may further include one or more of a wetting agent, detergent, enzyme cofactor and combinations thereof. Also provided are electrochemical test strips that include the subject reagent compositions, systems and kits that include the same as well as methods for using the same in analyte detection assays. The subject invention finds use in a variety of different applications, including glucose concentration determination applications.

DESCRIPTION OF THE SPECIFIC EMBODIMENTS

Figure 1:
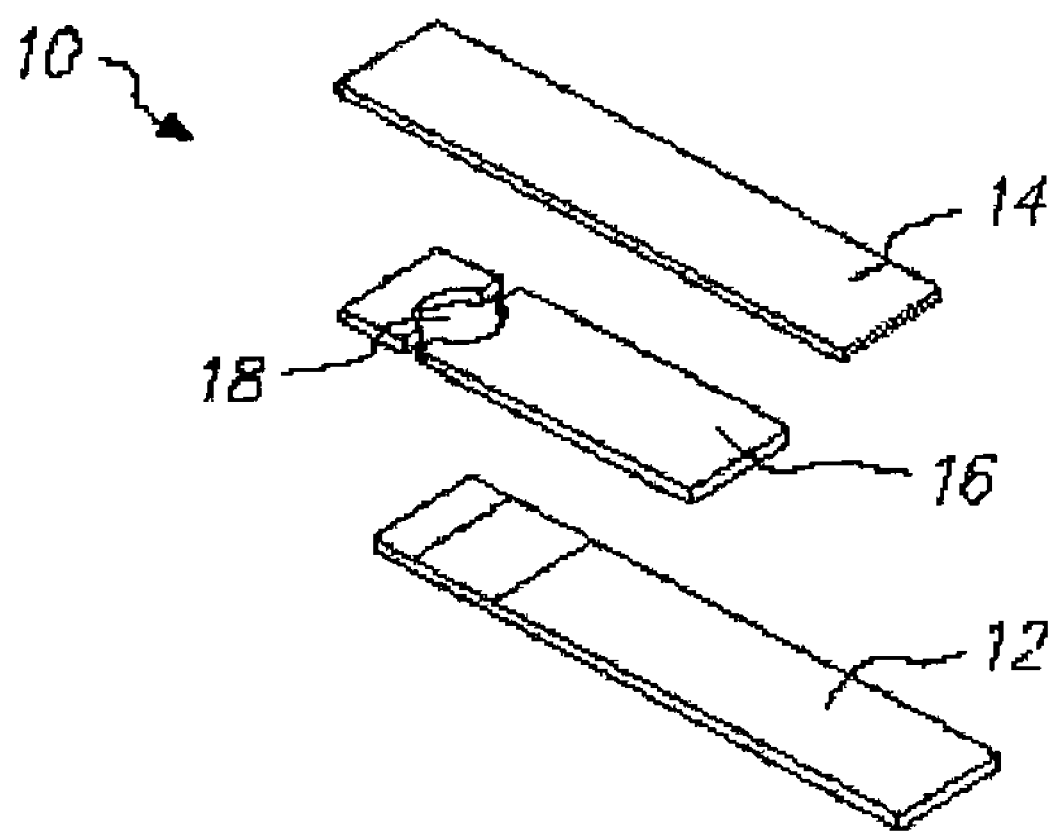
FIG. 1 provides an exploded view of an electrochemical test strip according to the present invention.

Mediator stabilized reagent compositions and methods for their use in electrochemical analyte determination assays are provided. The subject reagent compositions include an enzyme, a redox mediator and a mediator-stabilizing buffer. Optionally, the reagent compositions may further include one or more of a wetting agent, detergent, enzyme cofactor and combinations thereof. Also provided are electrochemical test strips that include the subject reagent compositions, systems and kits that include the same as well as methods for using the same in analyte detection assays. The subject invention finds use in a variety of different applications, including glucose concentration determination applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, and methodologies, which are described in the publications, which might be used in connection with the presently described invention.

As summarized above, the subject invention provides mediator stabilized electrochemical reagent compositions and methods for their use in electrochemical analyte detection applications. In further describing the subject invention, the subject reagent formulations are described first in greater detail, followed by a review of electrochemical reagent test strips that include the subject formulations and methods of using the same to electrochemically detect the present of an analyte, e.g., quantitatively, in a sample. Finally, a review of representative systems and kits according to the subject invention is also provided.

Mediator Stabilized Reagent Compositions

As summarized above, the subject invention provides mediator stabilized electrochemical reagent compositions. The subject electrochemical reagent compositions are compositions that find use in electrochemical analyte detection devices, e.g., test strips, and are typical redox reagent compositions. By mediator stabilized reagent composition is meant a composition in which the mediator component of the composition does not convert to a reduced form for an extended period of time under typical storage conditions. By typical storage conditions is meant at a temperature ranging from about −20 to about 55, usually from about 5 to about 40° C. and humidity ranging from about 5 to about 90%, usually from about 10 to about 60%. The subject mediator stabilized reagent compositions are stable for storage periods ranging from about greater than 18 months.

The subject mediator stabilized electrochemical reagent compositions according to the subject invention include at least the following components: an enzyme, a redox mediator and a mediator-stabilizing buffer. The subject redox reagent compositions may further include one or more additional components, including wetting agents, detergents, enzyme cofactors, and the like. Each of these components is now described separately in greater detail.

Enzyme Component

The enzyme component of the subject reagent compositions is, in many embodiments, an enzyme or plurality of enzymes that work in concert to oxidize the analyte of interest. In other words, the enzyme member may be made up of a single analyte oxidizing enzyme or a collection of two or more enzymes that work in concert to oxidize the analyte of interest, allowing generation of the electrochemical signal detected. Enzymes of interest include oxidases, dehydrogenases, lipases, kinases, diaphorases, quinoproteins and the like.

The enzyme selected in the reaction depends on the particular analyte for which the electrochemical test strip comprising the enzyme is designed to detect. Representative enzymes include: glucose oxidase, glucose dehydrogenase, cholesterol esterase, cholesterol oxidase, lipoprotein lipase, glycerol kinase, glycerol-3-phosphate oxidase, lactate oxidase, lactate dehydrogenase, pyruvate oxidase, alcohol oxidase, bilirubin oxidase, uricase, and the like.

Redox Mediator

Another component of the reagent composition is a redox mediator, which may comprise one or more mediator agents. The mediator acts an intermediary that facilitates the transfer of electrons from the enzyme (which has taken one or more electrons from the analyte during analyte oxidation) to the electrode. A variety of different mediator agents known in the art may be used, including ferricyanide, phenazine ethosulphate, phenazine methosulfate, phenylenediamine, N,N,N',N'-tetramethyl phenylenediamine, 1-methoxy-phenazine methosulfate, 2,5-dimethyl-1,4-benzoquinone, 2,6-dimethyl-1,4-benzoquinone, 2,5-dichloro-1,4-benzoquinone, ferrocene derivatives, osmium bipyridyl complexes, ruthenium complexes and the like. In many embodiments, the redox mediator is ferricyanide.

Mediator Stabilizing Buffer Component

Another component of the reagent composition is a mediator stabilizing buffering component. The subject mediator stabilizing buffering components may be made up of one or more, e.g., two, three, four or more, distinct buffering agents, where the buffering component stabilizes the mediator during storage of the composition in dry form such that little if any of the mediator is reduced prior to use, e.g., during storage. A buffer is considered to stabilize a mediator if, in the presence of the buffer, little if any of the mediator converts to a reduced form over a given storage period, as described above. Suitable buffers are buffers that do not cause the background signal in an electrochemical test to increase over time, as determined using the assays described in the Experimental Section, below. The background signal is the signal obtained when analyte free sample is introduced to the electrochemical testing system.

The buffering component, when present in a fluid reaction mixture prepared by combining the reagent composition with the sample to be assayed, is a component that maintains the pH of the reaction mixture at an acceptable range, where in many embodiments the buffering component maintains the pH range of the reaction mixture at a value ranging from about 4.0 to 8.0, for example from about 5.0 to about 7.5, such as from about 5.5 to about 7.0.

The one or more buffering agents of the buffering component have a pKa that provides for the above recited pH range in reaction mixtures prepared with the subject reagent formulations. Suitable buffering agents typically have pKa values of about 4 to about 8, for example from about 4.5 to about 7.5 including from about 5.0 to 7.0, including from about 5.5 to 7.0. Certain types of buffering agents may have more than one pKa value, and such types of agents may be employed, so long as at least one of their pKa values falls within the above-described ranges.

The buffering agents employed in the subject reagent compositions should have little, if any, binding affinity for divalent metal cations, e.g., $Ca^{2+}$, $Mg^{2+}$, etc., such that they have a low propensity to produce polydentate binding complexes with divalent metal cations. A given buffering agent is considered to have a low binding affinity for divalent metal cations if its binding affinity for divalent metal cations is less than the binding affinity of any enzyme/cofactor complex in the reaction mixture for the same divalent metal cations, where the binding affinity of suitable buffering agents is typically at least about 2-fold, usually at least about 5-fold and more usually at least about 10-fold, e.g., 25-fold, 50-fold, etc., less than the binding affinity of any enzyme/ cofactor complex in the reaction mixture for the same divalent metal cation. The stability constant for the complexation of suitable buffering agents to divalent metal cations, particularly $Ca^{2+}$, as measured using the assay described in Annali di Chimica, volume 73, (1983), p. 619 typically does not exceed about 1500, usually does not exceed about 100 and more usually does not exceed about 5 $mol^{-1}$ $dm^3$.

In certain embodiments, the buffering agents are small organic molecules. By small is meant that the molecular weight of the subject agents does not exceed about 5,000 daltons, and typically does not exceed about 2,500 daltons and more typically does not exceed about 1,000 daltons, where in many embodiments the molecular weight of the buffering agents ranges from about 50 to 750 daltons, e.g., from about 75 to 500 daltons.

In one embodiment, the buffer agents are polycarboxylic acids. By polycarboxylic acids is meant that the buffering agents include two or more carboxylic; acid functional moieties, where the number of different carboxylic acid functional moieties may range from about 2 to about 10, e.g., from about 2 to about 8, including from about 2 to about 6. The carboxylic acid groups or functional moieties of the subject buffering agents may be attached to a number of different structures, including aliphatic, alicyclic, aromatic and heterocyclic structures. The presence of more than one carboxylic acid group can have the beneficial effect of providing at least one pKa value for the buffer in the desired range.

In many embodiments, the two or more carboxylic groups of the subject polycarboxylic buffering agents are configured such that they sterically hinder the polydentate binding of divalent metal ions, such as $Ca^{2+}$ and the like. For example, buffering agents having two or more carboxylic acid groups positioned in a cis-position on a stable backbone that does not permit movement of the cis-groups relative to each other, e.g., one on ethylene backbone, etc., are of interest, where the stable backbone may be part of a larger structure, e.g., an aromatic ring, etc.

In certain embodiments the buffering agents are described by the following formula:

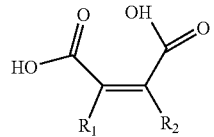

where $R_1$ and $R_2$ are independent H or organic moieties of one or more carbon atoms, which may be linear or branched and substituted with one or more heteroatoms, where $R_1$ and $R_2$ may be taken together to form a ring structure, e.g., an aromatic ring structure, and the like.

Specific polycarboxylic acids of interest include, but are not limited to: mellitic acid, citraconic acid, maleic acid, and the like, etc.

With respect to the above buffering agents, the buffering agents may be present in the subject reagent formulations as their free acids or salts thereof, or both.

A feature of the subject buffering component is that that the agent(s) that makes up the buffering component is present in an amount sufficient to provide for the mediator stabilizing capacity, as described above. In fluid compositions of the subject reagent formulations, the concentration of the buffering component typically ranges from about 0.1 to about 1000 mM, e.g., from about 0.5 to 500 mM. In certain embodiments, the buffer component is present at a low concentration, e.g., from about 0.5 to about 250 mM, usually from about 0.5 to about 100 mM. In certain embodiments, the buffer component is present at a higher concentration, e.g., from about 50 to about 500 mM. Where the reagent composition is a dry reagent formulation, e.g., as may be present in an electrochemical test strip as described in greater detail below, the amount of buffering component present in the dry composition typically ranges from about 0.01 to about 40.00, usually from about 1 to about 10% wt/wt.

Optional Components

As indicated above, the reagent composition may further include one or more of the following additional components: a wetting agent, detergent, coenzyme, enzyme cofactor, stabilizer, viscosity modifier or combinations thereof.

Wetting Agent and Detergents

A wetting agent may be added, in some embodiments in combination with a detergent, to the reagent composition to facilitate uniform coating of the reagent composition onto an electrochemical test strip. A plurality of one or more of the combination of agents may also be used. The agents used may improve dissolution of the assay reagents as well as enhance the wicking properties of a capillary fill strip. The agents include those known in the art, for example, polymers, anti-foaming agents, and surfactants. Representative types of surfactants/detergents of interest include, but are not limited to: Tritons, Macols, Tetronics, Silwets, Zonyls, and Pluronics. Suitable agents include Pluronic materials which are block co-polymers of polyethylene oxide and polypropylene oxide. Examples of Pluronic materials include Pluronic P103 which has good wetting properties and Pluronic F87 Prill which has good detergent properties. Both Pluronic P103 and F87 Prill also have a cloud point temperature greater than 80° C. which is desirable since this property avoids a phase change in the composition during the drying process.

Enzyme Coenzymes

Coenzymes which activate the enzyme component of the subject formulations may also be added to the reagent composition, where desired. An example of a coenzyme of interest is pyrroloquinoline quinone (PQQ). Other cofactors of interest include, but are not limited to: nicotinamide adenine dinucleotide (NAD), flavin adenine dinucleotide (FAD), cytochrome, and the like, depending on the type of enzyme applied to the test reagent.

Enzyme Cofactors

In certain embodiments, the subject compositions further include one or more enzyme cofactors. Enzyme cofactors of interest include divalent metal cations, e.g., $Ca^{2+}$, $Mg^{2+}$, etc.

Stabilizers

Stabilizers may also be added to the reagent composition to help stabilize the enzyme and prevent denaturation of the protein. The stabilizer may also help stabilize the redox state of the mediator, in particular, the oxidized redox mediator. Examples of stabilizing agents include, but are not limited to: carbohydrates (e.g., sucrose, trehalose, mannitol, and lactose), amino acids, proteins (such as BSA and albumin) and organic compounds such as EDTA and the like.

Viscosity Modifiers

Viscosity modifiers may also be added to the reagent to modify the liquid reagent rheology. Examples of such agents include poly(acrylic acid), poly(vinyl alcohol), dextran, BSA and the like.

Additional Features

The reagent composition may be present in a dry or liquid form. The amounts of the various components as described above may vary, and the following specifically provided amounts are provided for illustration purposes only.

In liquid formulations of the subject reagent compositions, the enzyme component is typically present in a concentration ranging from about 35 to about 450, usually from about 130 to about 270 µM. The mediator is typically present in an amount ranging from about 250 to about 1000, usually from about 500 to about 1000 mM. The stabilizing buffer component is present in ranges as provided above. The concentration of any coenzymes typically ranges from about 60 to about 670 µM, usually from about 200 to about 430 µM. The concentration of any cofactors typically ranges from about 0.5 to about 5 mM.

In dry formulations, the amount of the enzyme component typically ranges from about 1.5 to about 15, usually from about 5 to about 10% dry wt/wt. The mediator is typically present in an amount ranging from about 60 to about 85, usually from about 75 to about 85% dry wt/wt. The stabilizing buffer component is present in ranges as provided above. The amount of any coenzymes typically ranges from about 0.01 to about 0.1, usually from about 0.03 to about 0.06% dry wt/wt. The amount of any cofactors typically ranges from about 0.02 to about 0.2% dry wt/wt.

Representative Specific Formulation of Interest:

In a representative specific formulation of interest, the formulation includes glucose dehydrogenase as the enzyme and PQQ as a coenzyme. Also present is an enzyme cofactor $Ca^{2+}$. In these formulations, PQQ binds with GDH and $Ca^{2+}$ to form the activated enzyme, or holo-enzyme. It is known that two PQQ molecules per GDH dimer molecule are required to fully activate the enzyme. In some embodiments, the mole ratio of PQQ to GDH in the reagent compositions is between about 2 to about 4. In further embodiments, the mole ratio of PQQ to GDH is between about 2.2 to about 2.5. The activity of the GDH-PQQ holoenzyme in these representative formulations typically ranges from about 10 to 1000 kU/ml, usually at least about 50 to 300 kU/ml. The enzyme activity is determined using a spectrophotometric assay performed at 30° C. Typically, the 3 parts enzyme solution is mixed to 100 parts substrate solution. Next, the absorbance is monitored at 600 nm over a 5-second period. The substrate solution comprises 112 mM glucose, 2 mM phenazine ethosulfate, 60 nM 2,6-dichloroindophenol, and 50 mM piperazine, N,N' bis-(2-ethanesulfonic acid) (PIPES) at pH 6.8. The enzyme solution comprises about 0.25 to 0.50 mg/mL GDH, 1.25 µM PQQ, 1.25 mM $CaCl_2$, 0.1% (w/v) bovine serum albumin, and 50 mM PIPES at pH 6.8. The amount of $Ca^{2+}$, e.g., as provided by $CaCl_2$, typically ranges from about 0 to 10 mM. The mediator in this specific formulation of interest is ferricyanide, which is typically present in amounts ranging from about 0.1 to 10 M, usually from about 0.3 to about 1.0 M. When present, the wetting agent/detergent component is present in an amount ranging from about 0.01 to 1.0% wt/wt. Sucrose, when present, is present in an amount ranging from about 10 to about 1000 mM. The buffering agents of specific interest are citraconic acid and or? mellitic acid, and these are present in the ranges provided above.

Electrochemical Cells

Figure 2:
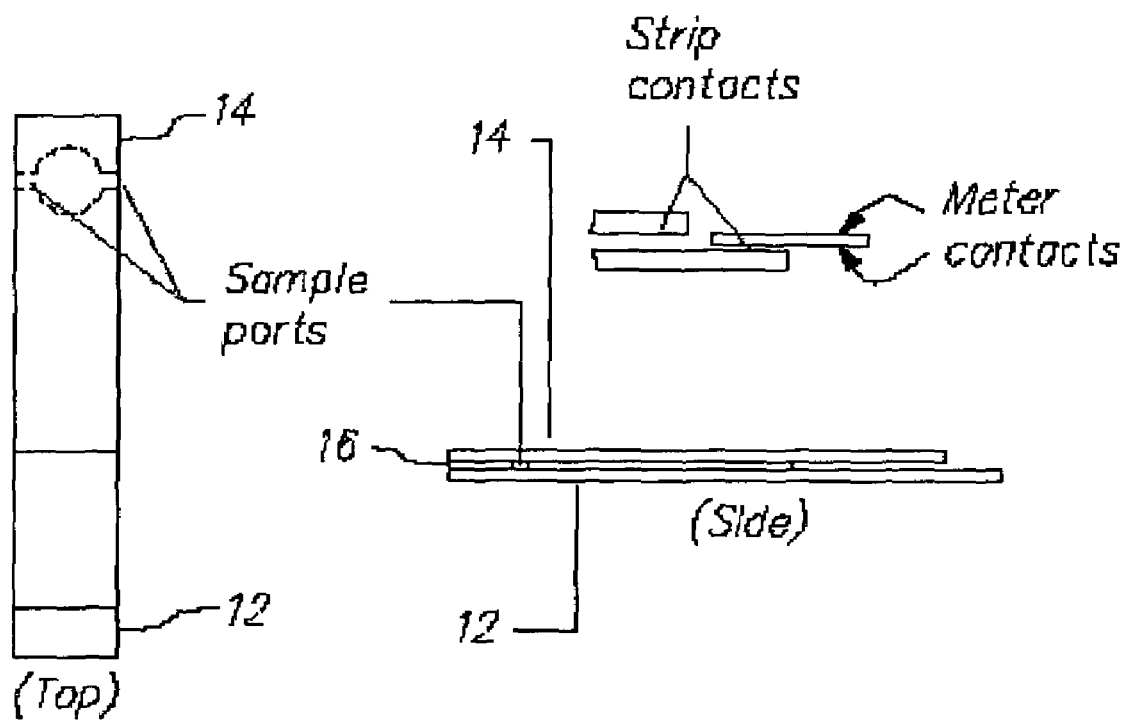
FIG. 2 shows the same test strip in assembled form.

As summarized above, also provided by the subject invention are electrochemical cells that include the subject reagent compositions. A variety of different types of electrochemical cell configurations are known, including those described in U.S. Pat. Nos.: 5,723,284; 5,834,224; 5,942,102; 5,972,199; 5,997,817; 6,083,710; 6,121,009; 6,134,461; and 6,193,873; the disclosures of which are herein incorporated by reference; as well as other patent documents: WO 99/49307; WO 97/18465; WO 01/57510; WO 01/57238; WO 02/48707; WO 02/50609; EP 0 969 097A2 and GB 2 304 628; the priority documents of which, where they are U.S. applications, are herein incorporated by reference. Any of these or other electrochemical cells known to those of skill in the art may be modified to incorporate the subject compositions:

In certain embodiments, the electrochemical cell is present in an electrochemical test strip. A representation of an electrochemical test strip according to the subject invention is provided in FIGS. 1 and 2. FIG. 1 provides an exploded view of an electrochemical test strip 10 which is made up of working electrode 12 and reference electrode 14 separated by spacer layer 16 which has a cutaway section 18 that defines the reaction zone or area in the assembled strip. FIG. 2 shows the same test strip in assembled form. Each of the various components are now described in greater detail below.

Electrodes

The subject electrochemical test strips comprising the reagent compositions include a working electrode and a reference electrode. Generally, the working and reference electrodes are configured in the form of elongated rectangular strips. Typically, the length of the electrodes ranges from about 1.9 to about 4.5 cm, usually from about 2 to about 2.8 cm. The width of the electrodes ranges from about 0.38 to about 0.76 cm, usually from about 0.51 to about 0.67 cm. The reference electrodes typically have a thickness ranging from about 10 to 100 nm and usually from about 18 to about 22 nm. In certain embodiments, the length of one of the electrodes is shorter than the length of the other electrode, wherein in certain embodiments it is about 0.32 cm shorter.

The working and reference electrodes are further characterized in that at least the surface of the electrodes that faces the reaction area in the strip is a conductive material, e.g., a metal or other conductive material, where representative materials of interest include, but are not limited to: palladium, gold, platinum, silver, iridium, carbon, doped tin oxide, stainless steel and the like. In certain embodiments, the conductive material is gold or palladium. While in principle the entire electrode may be made of the conductive material, each of the electrodes is generally made up of an inert support material on the surface of which is present a thin layer of the conducting material component of the electrode. Any convenient inert backing material may be employed in the subject electrodes, where typically the material is a rigid material that is capable of providing structural support to the electrode and, in turn, the electrochemical test strip as a whole. Suitable materials that may be employed as the backing substrate include plastics, e.g. PET, PETG, polyimide, polycarbonate, polystyrene, silicon, ceramic, glass, and the like.

Spacer Layer

A feature of the subject electrochemical test strips is that the working and reference electrodes as described above face each other and are separated by only a short distance, such that the distance between the working and reference electrode in the reaction zone or area of the electrochemical test strip is extremely small. This minimal spacing of the working and reference electrodes in the subject test strips is a result of the presence of a thin spacer layer positioned or sandwiched between the working and reference electrodes. The thickness of this spacer layer generally ranges from about 1 to about 500 μm, usually from about 100 to about 200 μm. The spacer layer is cut so as to provide a reaction zone or area with at least an inlet port into the reaction zone, and generally an outlet port out of the reaction zone as well. A representative spacer layer configuration can be seen in FIGS. 1 and 2. While the spacer layer is shown in these figures as having a circular reaction area cut with side inlet and outlet vents or ports, other configurations are possible, e.g. square, oval, triangular, rectangular, irregular shaped reaction areas, etc. The spacer layer may be fabricated from any convenient material, where representative suitable materials include PET, PETG, polyimide, polycarbonate and the like, where the surfaces of the spacer layer may be treated so as to be adhesive with respect to their respective electrodes and thereby maintain the structure of the electrochemical test strip. Of particular interest is the use of a die-cut double-sided adhesive strip as the spacer layer.

Reaction Zone

The subject electrochemical test strips include a reaction zone or area that is defined by the working electrode, the reference electrode and the spacer layer, where these elements are described above. Specifically, the working and reference electrodes define the top and bottom of the reaction area, while the spacer layer defines the walls of the reaction area. The volume of the reaction area is at least about 0.1 μl, usually at least about 1 μl and more usually at least about 1.5 μl, where the volume may be as large as 10 μl or larger. As mentioned above, the reaction area generally includes at least an inlet port, and in many embodiments also includes an outlet port. The cross-sectional area of the inlet and outlet ports may vary as long as it is sufficiently large to provide an effective entrance or exit of fluid from the reaction area, but generally ranges from about $9\times10^{-5}$ to about $5\times10^{-3}$ cm$^2$, usually from about $5\times10^{-4}$ to about $2.5\times10^{-3}$ cm$^2$.

Present in the reaction zone is a reagent formulation according to the present invention, where the reagent formulation is typically present in a dry format.

Analyte Detection Methods

Also provided by the subject invention are methods of using the subject reagent compositions to determine the concentration of an analyte in a physiological sample. For convenience, the methods are described in terms of the above representative test strips. However, the invention is not limited thereto, as any method of detecting an analyte using the subject reagent formulations in an electrochemical cell is encompassed within the invention.

The methods include applying the sample to an electrochemical test strip that includes the reagent compositions of the subject invention, detecting an electrical signal generated by the test strip and relating the detected electrical signal to the concentration of the analyte in the sample. A variety of different analytes may be detected using the subject test strips, where representative analytes include glucose, cholesterol, lactate, alcohol, and the like. In many preferred embodiments, the subject methods are employed to determine the glucose concentration in a physiological sample. While in principle the subject methods may be used to determine the concentration of an analyte in a variety of different physiological samples, such as urine, tears, saliva, and the like, they are particularly suited for use in determining the concentration of an analyte in blood or blood fractions, and more particularly in whole blood.

In practicing the subject methods, the first step is to introduce a quantity of the physiological sample into the reaction area of the test strip, where the electrochemical test strip is described supra. The amount of physiological sample, e.g. blood, that is introduced into the reaction area of the test strip may vary, but generally ranges from about 0.05 to about 10 ul, usually from about 0.5 to about 1.6 ul. The sample may be introduced into the reaction area using any convenient protocol, where the sample may be injected into the reaction area, allowed to wick into the reaction area, and the like, as may be convenient.

Following application of the sample to the reaction zone, an electrochemical measurement is made using the reference and working electrodes. The electrochemical measurement that is made may vary depending on the particular nature of the assay and the device with which the electrochemical test strip is employed, e.g. depending on whether the assay is coulometric, amperometric or potentiometric. Generally, the electrochemical measure will measure charge (coulometric), current (amperometric) or potential (potentiometric), usually over a given period of time following sample introduction into the reaction area. Methods for making the above described electrochemical measurement are further described in U.S. Pat. Nos.: 4,224,125; 4,545,382; and 5,266,179; as well as WO 97/18465; WO 99/49307; the disclosures of which are herein incorporated by reference.

Following detection of the electrochemical signal generated in the reaction zone as described above, the amount of the analyte present in the sample introduced into the reaction zone is then determined by relating the electrochemical signal to the amount of analyte in the sample. In making this derivation, the measured electrochemical signal is typically compared to the signal generated from a series of previously obtained controls or standard values, and determined from this comparison. In many embodiments, the electrochemical signal measurement steps and analyte concentration derivation steps, as described above, are performed automatically by a device designed to work with the test strip to produce a value of analyte concentration in a sample applied to the test strip. A representative reading device for automatically practicing these steps, such that user need only apply sample to the reaction zone and then read the final analyte concentration result from the device, is further described in U.S. Pat. No. 6,193,873; the disclosure of which is herein incorporated by reference.

The methods may be employed to determine the concentration of a variety of different analytes, where representative analytes include glucose, cholesterol, lactate, alcohol, and the like. In many preferred embodiments, the subject methods are employed to determine the glucose concentration in a physiological sample. While in principle the subject methods may be used to determine the concentration of an analyte in a variety of different physiological samples, such as urine, tears, saliva, and the like, they are particularly suited for use in determining the concentration of an analyte in blood or blood fractions, e.g., blood derived samples, and more particularly in whole blood.

Systems

Also provided by the subject invention are systems for use in the detection of analytes, where the systems include a reagent composition according to the subject invention, e.g., present in a test strip as described above, and a device for use in electrochemically assaying a sample using the subject reagent compositions.

The devices or meters of the subject systems are typically electrochemical measuring devices. The subject meters typically include: (a) a means for applying an electric potential to an electrochemical cell into which the sample has been introduced; (b) a means for measuring cell current in the cell; and (c) a means for relating the current to the concentration of analyte in the cell. Representative electrochemical meters or devices are described in U.S. Pat. Nos.: 5,723,284; 5,834,224; 5,942,102; 5,972,199; 5,997,817; 6,083,710; 6,121,009; 6,134,461; and 6,193,873; the disclosures of which are herein incorporated by reference; as well as other patent documents: WO 99/49307; WO 97/18465; WO 01/57510; WO 01/57238; WO 02/48707; WO 02/50609; EP 0 969 097A2 and GB 2 304 628.

Kits

Also provided by the subject invention are kits for use in practicing the subject methods. The kits of the subject invention include the reagent compositions as described above, where the compositions are often present in a test strip, as described above. The subject kits may further include an obtainment element for obtaining a physiological sample. For example, where the physiological sample is blood, the subject kits may further include an element for obtaining a blood sample, such as a lance for sticking a finger, a lance actuation means, and the like. In addition, the subject kits may include an analyte standard, e.g. a control solution that contains a standardized concentration of glucose. In certain embodiments, the kits also include an automated instrument, as described above, for use with the reagent compositions and test strips that include the same.

Finally, the kits may include instructions for using the subject compositions in the determination of an analyte concentration in a physiological sample. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

The following examples are offered by way of illustration and not by way of limitation.

EXPERIMENTAL

EXAMPLE 1

Glucose Linearity Results Using Citrate, Malic, and Tartarate

Figure 3:
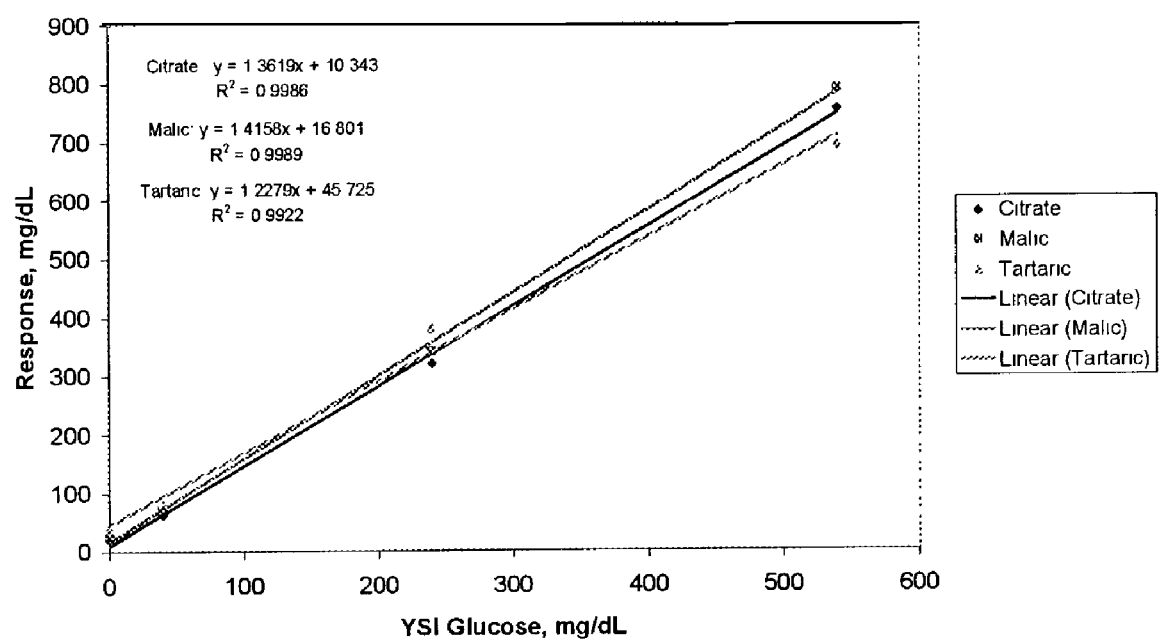
FIG. 3 provides the results of linearity test comprising citrate, malic and tartaric acid formulations according to the present invention.

Citric, malic, and tartaric buffer formulations were separately formulated at 100 mM concentration and pH 5.5. All 3 formulations also contained equivalent amounts of 0.1% anti-foam (RNA Equilibrator), 1 mM $CaCl_2$, PQQ (2× mole ratio to GDH), 200 mM potassium ferricyanide, and 45 mg/mL GDH. Each formulation was ink-jetted onto a Pd substrate. The sensors were tested with blood containing glucose using chronoamperometry by applying a potential of −0.3 V for 10 sec, and then applying a potential of +0.3 V for 5 sec. Testing with blood showed good linearity with glucose for all cases (FIG. 3). Background for citrate and malic buffers were comparable while that of tartaric buffer was higher. In addition, tartaric buffer formed an insoluble salt with $Ca^{2+}$ making it less desirable.

EXAMPLE 2

Glucose Linearity and Hematocrit Results Using Citrate and Mellitate

Figure 4:
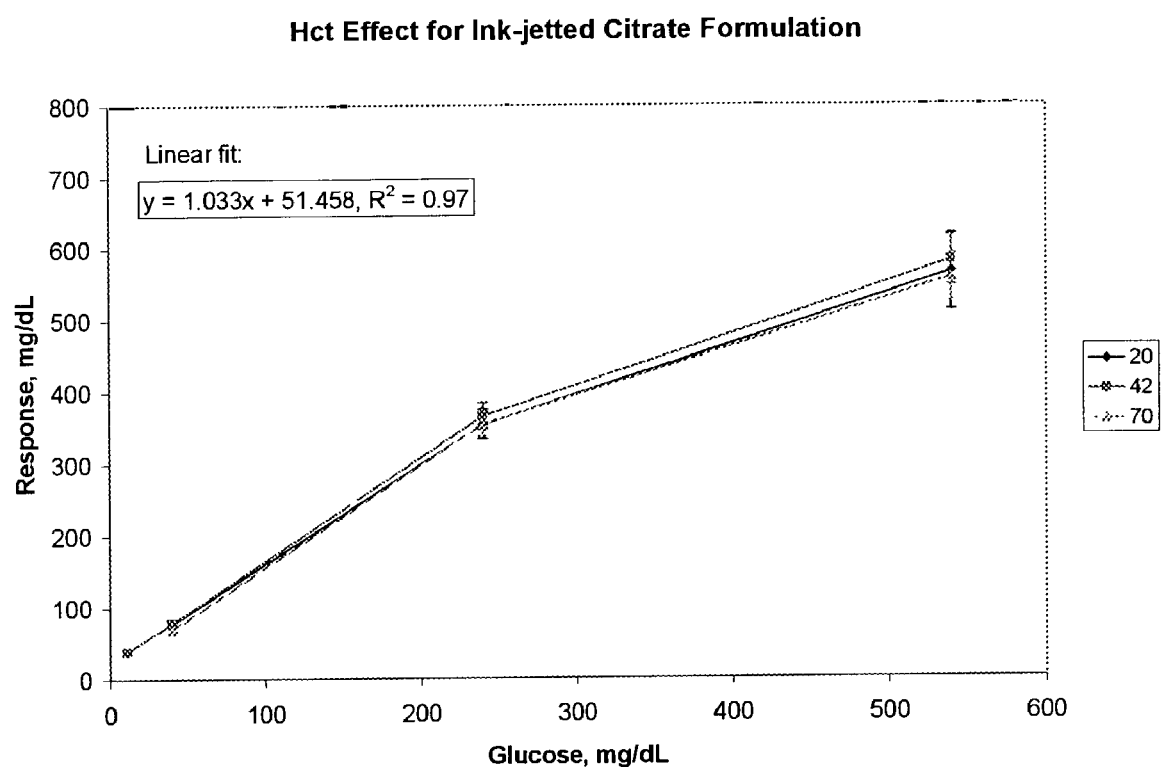
FIGS. 4 and 5 provide results showing the hematocrit effect for ink-jetted citrate and mellitic acid formulations according to the present invention.
Figure 5:
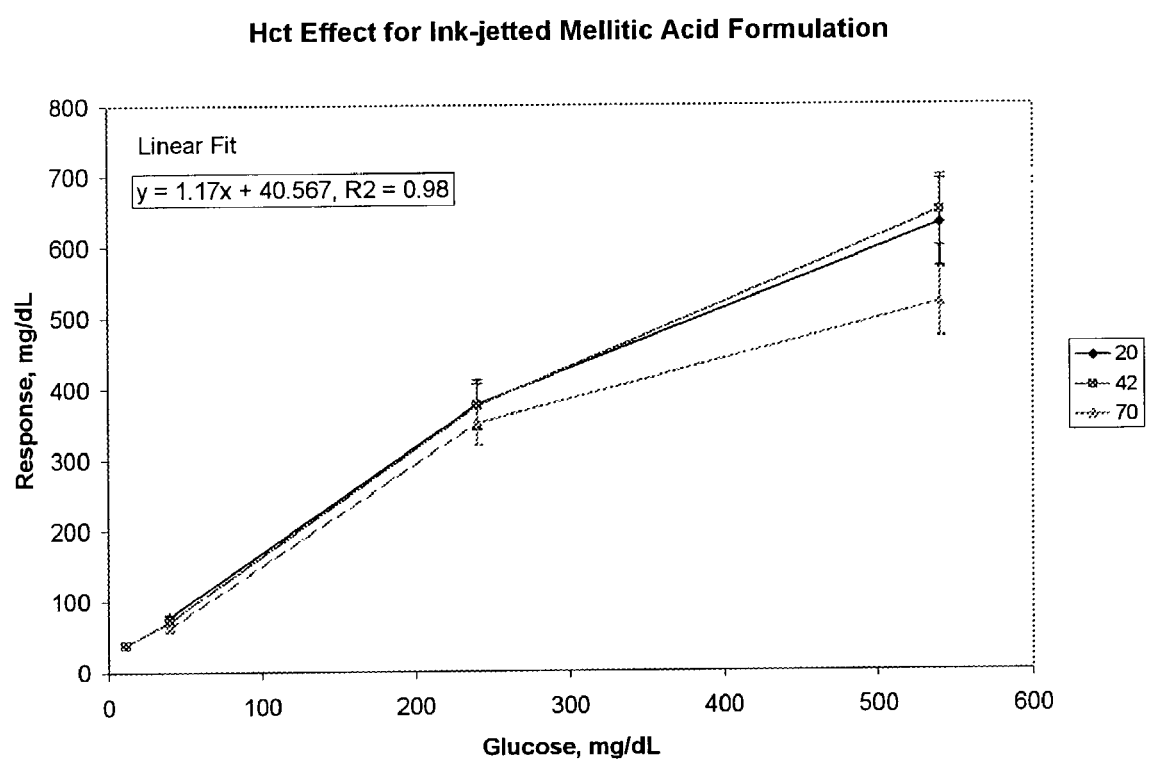

Citrate buffer was formulated at 400 mM and pH 5.5. Mellitate buffer was formulated at 160 mM and pH 6.4. Both formulations also contained equivalent amounts of 0.1% anti-foam (RNA Equilibrator), 1 mM $CaCl_2$, PQQ (2× mole ratio to GDH), 200 mM potassium ferricyanide, and 32 mg/mL GDH. Blood testing was conducted using three hematocrit levels (20, 42, and 70%) and 4 glucose levels (FIG. 4 and 5). The glucose response was not linear, but did increase with increasing glucose concentration. Hematocrit performance for citrate buffer was slightly better than mellitate. The results are provided in FIGS. 4 and 5.

EXAMPLE 3

Hematocrit and Stability Results Using Citrate and Citraconate

Figure 6:
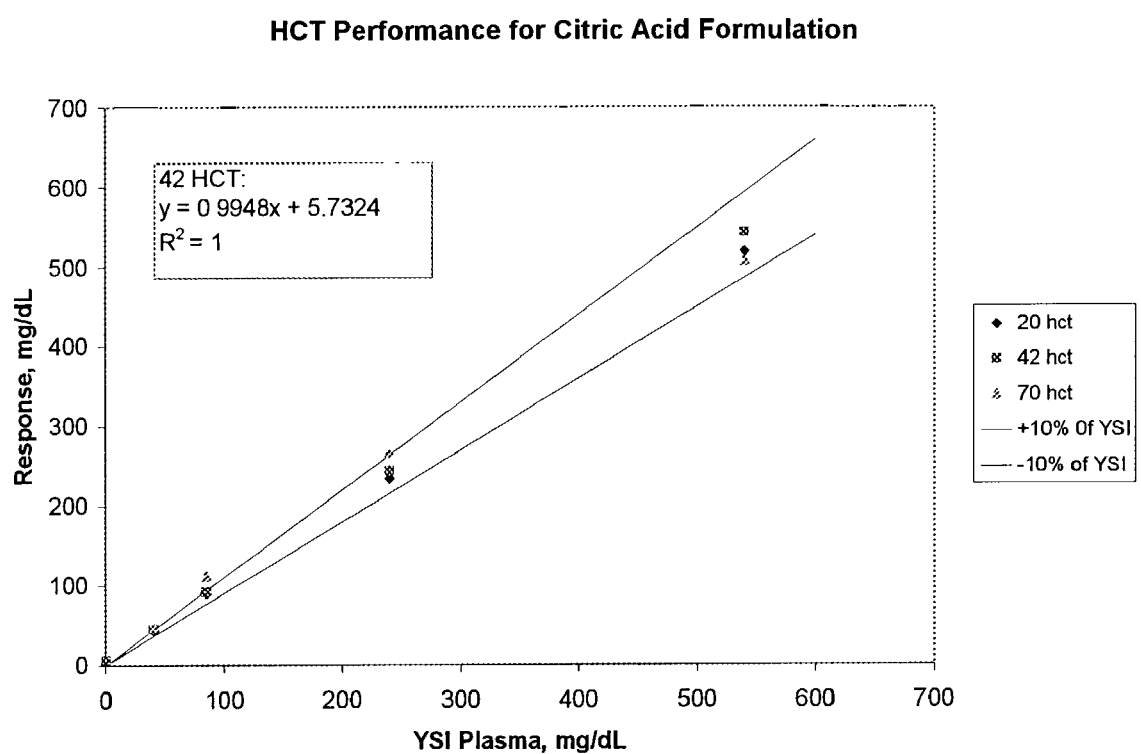
FIGS. 6 and 7 provide results showing the hematocrit performance for citric acid and citraconic acid reagent formulations according to the present invention.
Figure 7:
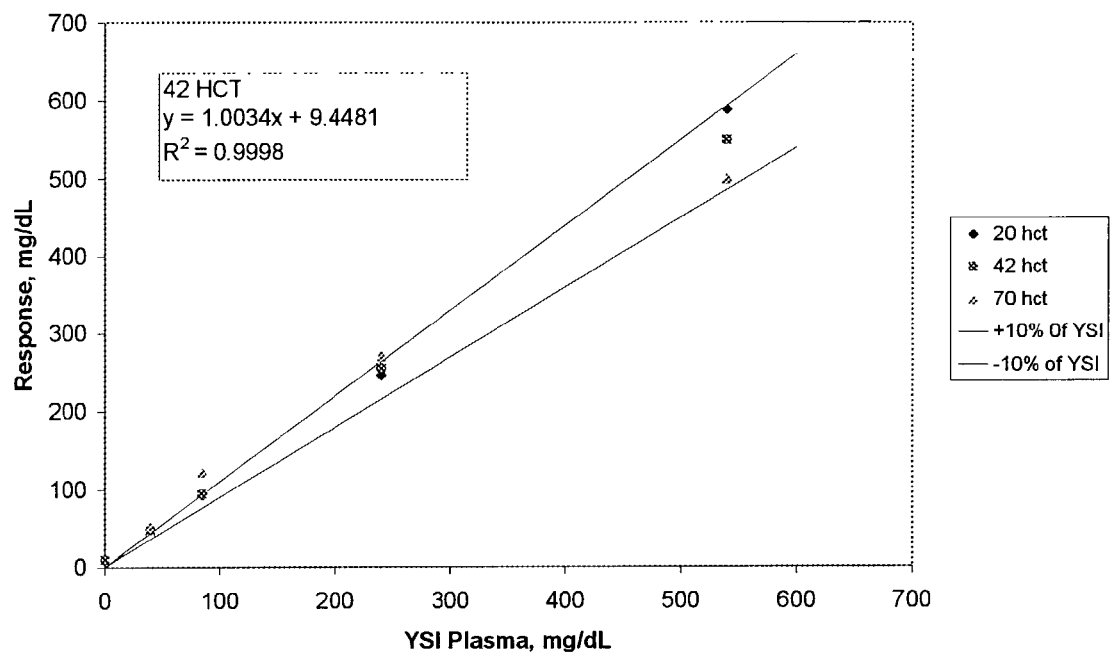

Citrate and citraconate buffers were separately formulated at 300 mM concentration and pH 6.5. Both formulations also contained equivalent amounts of 0.1% anti-foam (RNA Equilibrator), 4 mM $CaCl_2$, PQQ (2× mole ratio to GDH), 800 mM potassium ferricyanide, and 46 mg/mL GDH. Formulations were deposited on Pd by means of inkjetting. Hematocrit performance for both citrate and citraconate buffers were similar (FIGS. 6 and 7). Accelerated aging at 56° C. for 14 days showed that citraconate had excellent background and performance stability as compared to citrate (Table 1). The bias represented in Table 1 is given as an absolute response difference at the 40 mg/dL glucose concentration, and as a percentage bias for glucose concentration greater than 100 mg/dL.

TABLE 1

|  | CITRACONIC | | CITRATE | |
| --- | --- | --- | --- | --- |
| GLUCOSE LEVEL | Bias to YSI at Day 0 | Bias to YSI at Day 14 @ 56 C. | Bias to YSI at Day 0 | Bias to YSI at Day 14 @ 56 C. |
| 40 | 6.98 | 5.38 | 4.57 | −7.06 |
| 240 | 6.52 | 3.69 | 1.44 | −25.77 |
| 540 | 0 | 1.45 | 0 | −35.35 |

EXAMPLE 4

Linearity and Stability Results Using Citraconate and Maleic

Figure 8:
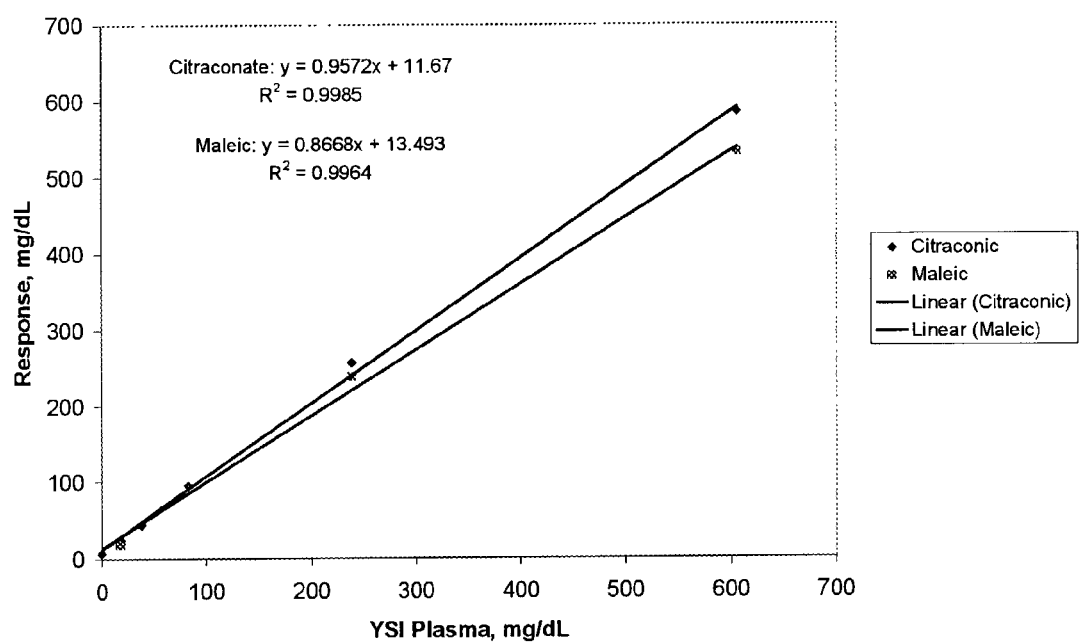
FIG. 8 provides results of a linearity test for citraconic and maleic acid reagent formulations according to the present invention.

Citraconate and maleic buffers were separately formulated at 300 mM concentration and pH 6.5. Both formulations also contained equivalent amounts of 0.066% Pluronic 25R2, 0.033% Pluronic L62, 4 mM $CaCl_2$, PQQ (2× mole ratio to GDH), 800 mM potassium ferricyanide, and 26 mg/mL GDH. Formulations were deposited on Pd by means of inkjetting. Initial performance testing with nominal hematocrit showed good linearity (FIG. 8). Stability data indicated stable background in both cases; however, performance for maleic buffer formulation degraded at the high glucose levels—an indication of enzyme instability (Table 2).

TABLE 2

| GLUCOSE LEVEL | CITRACONIC | | CITRATE | |
| --- | --- | --- | --- | --- |
| | Bias to YSI at Day 0 | Bias to YSI at Day 14 @ 56 C. | Bias to YSI at Day 0 | Bias to YSI at Day 14 @ 56 C. |
| 40 | 6.17 | 4.52 | 0.03 | −0.93 |
| 240 | 7.29 | 3.93 | −0.26 | −10.93 |
| 540 | −3.41 | −0.08 | −12.20 | −25.37 |

EXAMPLE 5

Hematocrit and Stability Results Using Citraconate and Mellitic Buffers

Figure 9:
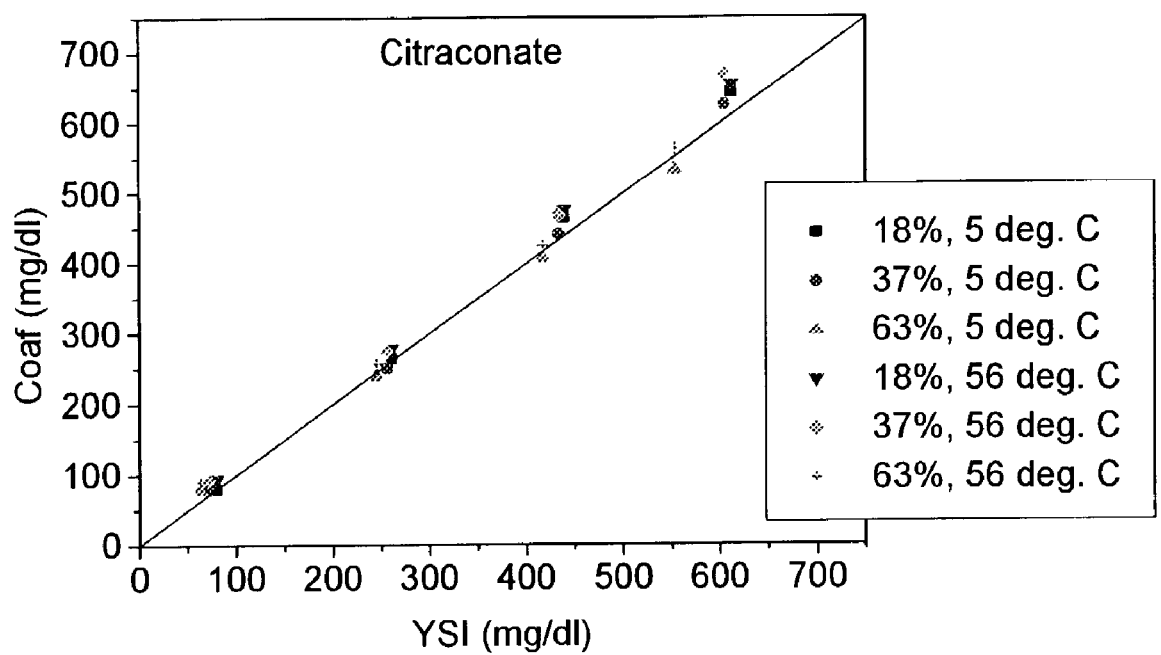
FIGS. 9 and 10 show stability data for electrochemical glucose sensors made with the citraconate and mellitate reagent formulations according to the present invention.
Figure 10:
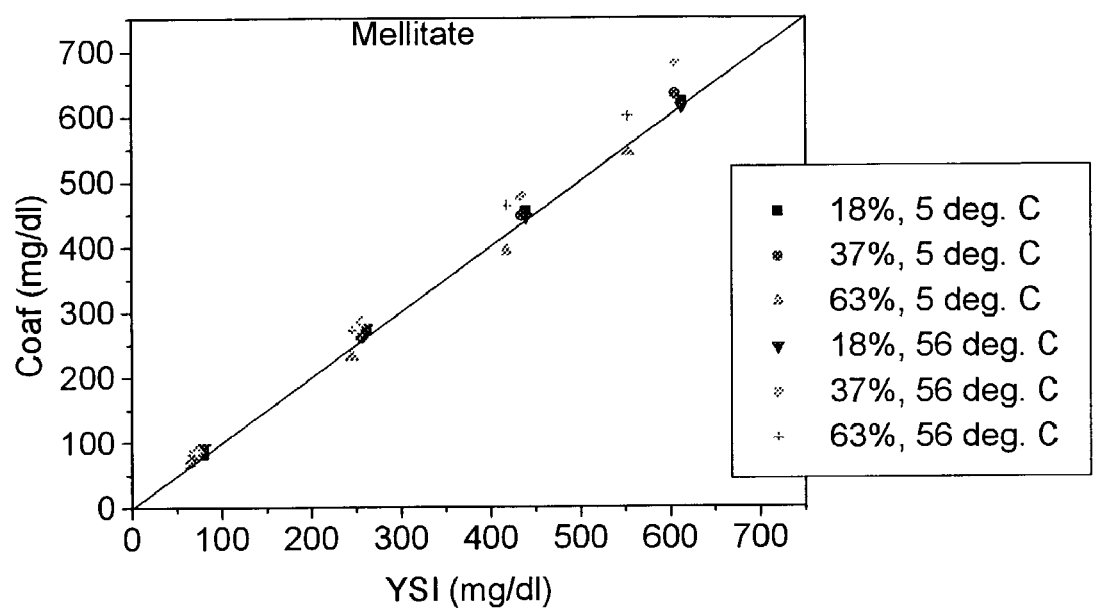

Strips were made in a manner similar to Example 4 except that the reagent was deposited by a manual pipette and dried under a hot plate with a hot air stream. FIGS. 9 and 10 show the stability data for glucose sensors made with citraconate and mellitate buffers. A pH of 6.5 was chosen with a buffer concentration of 105 and 40 mM for mellitic acid and citraconic acid, respectively. The sensors were stored at 5° C. or 56° C. for 2 weeks and then tested with 18, 37 and 63% hematocrit blood.

The above results and discussion demonstrate that the present invention provides electrochemical reagent compositions in which the mediator is storage stabilized. Advantages of the subject invention include more accurate results, as well as obviation of the need to include less desirable stabilizing agents and/or perform a burn and read protocol. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A dry reagent composition comprising:
an enzyme;
a redox mediator;
an enzyme cofactor; and
a mediator-stabilizing buffer comprising a polycarboxylic acid having more than two carboxylic acid groups, present in an amount in the range of 0.01% wt/wt to 40% wt/wt sufficient to stabilize said redox mediator during storage of the dry reagent composition, wherein said mediator-stabilizing buffer has a low binding affinity for divalent metal ions, said low binding affinity for divalent metal ions being at least 2-fold less than a divalent metal ion binding affinity of an enzyme/cofactor complex formed from the enzyme and the cofactor of the dry reagent mixture.

2. The dry reagent composition according to claim 1, wherein said buffer has a pKa ranging from about 5 to about 8.

3. The dry reagent composition according to claim 2, wherein said buffer has a pKa ranging from about 6 to about 7.

4. The dry reagent composition according to claim 1, wherein said buffer is formulated to have a pH in the range from about 4 to 8.

5. The dry reagent composition according to claim 4, wherein said buffer is formulated to have a pH in the range from about 6 to 7.

6. The dry reagent composition according to claim 1, wherein at least two of said carboxylic groups are present in a cis formation.

7. The dry reagent composition according to claim 6, wherein at least two of said carboxylic groups present in a cis formation are bonded to an ethylene moiety.

8. The dry reagent composition according to claim 7, wherein said polycarboxylic acid is mellitic acid and salts thereof.

9. The dry reagent composition according to claim 1, wherein said enzyme is an oxidizing enzyme.

10. The dry reagent composition according to claim 9, wherein said oxidizing enzyme is chosen from an oxidase and a dehydrogenase.

11. The dry reagent composition according to claim 9, wherein said enzyme is a dehydrogenase.

12. The dry reagent composition according to claim 9, wherein said oxidizing enzyme is a glucose oxidizing enzyme.

13. The dry reagent composition according to claim 1, wherein said mediator is ferricyanide.

14. The dry reagent composition according to claim 1, wherein said reagent composition further comprises a stabilizer.

15. The dry reagent composition according to claim 14, wherein said stabilizer is a carbohydrate.

16. The dry reagent composition according to claim 15, wherein said carbohydrate is sucrose.

17. The reagent composition according to claim 1, wherein said polycarboxylic acid has from 3 to 10 carboxylic acid groups.

18. An electrochemical cell comprising a dry reagent composition that includes:
an enzyme;
a redox mediator;
an enzyme cofactor; and
a mediator-stabilizing buffer comprising a polycarboxylic acid having more than two carboxylic acid groups, present in an amount of range of 0.01% wt/wt to 40% wt/wt sufficient to stabilize said redox mediator during storage of the dry reagent composition, wherein said mediator-stabilizing buffer has a low binding affinity for divalent metal ions, said low binding affinity for divalent metal ions being at least 2-fold less than a divalent metal ion binding affinity of an enzyme/cofactor complex formed from the enzyme and the cofactor of the dry reagent mixture.

19. The electrochemical cell according to claim 18, wherein said cell is present in an electrochemical test strip.

20. A method for making an electrochemical test strip, the method comprising:
making an electrochemical strip that includes:
a dry reagent composition with:
an enzyme;
a redox mediator;
an enzyme cofactor; and
a mediator-stabilizing buffer comprising a polycarboxylic acid having more than two carboxylic acid groups, present in an amount of range of 0.01% wt/wt to 40% wt/wt sufficient to stabilize said redox mediator during storage of the dry reagent composition, wherein said mediator-stabilizing buffer has a low binding affinity for divalent metal ions, said low binding affinity for divalent metal ions being at least 2-fold less than a divalent metal ion binding affinity of an enzyme/cofactor complex formed from the enzyme and the cofactor of the dry reagent mixture.

21. A method for determining the concentration of an analyte in a sample, said method comprising:
(a) applying said sample to an electrochemical cell comprising a dry reagent composition that includes:
an enzyme;
a redox mediator;
an enzyme cofactor; and
a mediator-stabilizing buffer comprising a polycarboxylic acid having more than two carboxylic acid groups, present in an amount of range of 0.01% wt/wt to 40% wt/wt sufficient to stabilize said redox mediator during storage of the dry reagent composition, wherein said mediator-stabilizing buffer has a low binding affinity for divalent metal ions, said low binding affinity for divalent metal ions being at least 2-fold less than a divalent metal ion binding affinity of an enzyme/cofactor complex formed from the enzyme and the cofactor of the dry reagent mixture;
(b) detecting an electrical signal produced by said cell; and
(c) relating said detected electrical signal to the concentration of said analyte in said sample.

22. A method according to claim 21, wherein said analyte is glucose.

23. A method according to claim 21, wherein said physiological sample is blood.

* * * * *